United States Patent [19]

Christian

[11] Patent Number: 4,673,657
[45] Date of Patent: Jun. 16, 1987

[54] MULTIPLE ASSAY CARD AND SYSTEM

[75] Inventor: Clifford N. Christian, Costa Mesa, Calif.

[73] Assignee: The Regents of the University of California, Berkeley, Calif.

[21] Appl. No.: 616,395

[22] Filed: Jun. 1, 1984

Related U.S. Application Data

[63] Continuation-in-part of Ser. No. 526,970, Aug. 26, 1983, abandoned.

[51] Int. Cl.[4] .................... G01N 33/53; G01N 33/543
[52] U.S. Cl. ...................................... 436/501; 422/58; 422/61; 422/63; 422/81; 435/301; 436/524; 436/530; 436/531; 436/807; 436/809
[58] Field of Search ............... 436/524, 530, 531, 805, 436/804, 809, 810, 501, 807; 435/301; 422/56, 58, 61, 63, 81

[56] References Cited

U.S. PATENT DOCUMENTS

| | | | |
|---|---|---|---|
| 3,925,166 | 12/1975 | Blume | 435/301 |
| 3,930,983 | 7/1975 | Sieber . | |
| 4,018,662 | 4/1977 | Ruhenstroth-Bauer . | |
| 4,111,754 | 9/1978 | Park . | |
| 4,172,117 | 10/1979 | Schober . | |
| 4,219,335 | 8/1980 | Ebersole . | |
| 4,237,096 | 12/1980 | Popoff et al. . | |
| 4,318,994 | 3/1982 | Meyer | 435/301 |
| 4,363,874 | 12/1982 | Greenquist . | |
| 4,378,344 | 3/1983 | Zahradnik et al. . | |
| 4,459,360 | 7/1984 | Marinkovich | 436/804 |
| 4,472,353 | 9/1984 | Moore | 422/56 |
| 4,514,508 | 4/1985 | Hirshfeld | 436/821 |
| 4,526,753 | 7/1985 | Boger | 422/56 |
| 4,537,861 | 8/1985 | Elings | 436/805 X |
| 4,591,570 | 5/1986 | Chang | 436/518 |

*Primary Examiner*—Sidney Marantz
*Attorney, Agent, or Firm*—Poms, Smith, Lande & Rose

[57] ABSTRACT

An assay card having a three-layer laminate construction in which various recessed channels and chambers are interconnected with protruding flexible chambers and channels to provide a completely self-contained analytical system adapted for treating and analyzing a sample utilizing a multiple assay rod. The configuration of the various channels and chambers are arranged so that a wide variety of analyses involving numerous steps can be accomplished using the card. The card is activated and analysis and/or treatment carried out by passing a roller bar or other pressure device over the top of the card to force solutions and reagents through the various card channels. In addition, the movement of the pressure bar over the card closes and opens various channels within the card to provide controlled and programmable transfer of solutions during treatment of the microassay rod. An assay rod having fluorescent marker layers is provided for use in analysis methods utilizing fluorescently marked detection substances.

27 Claims, 19 Drawing Figures

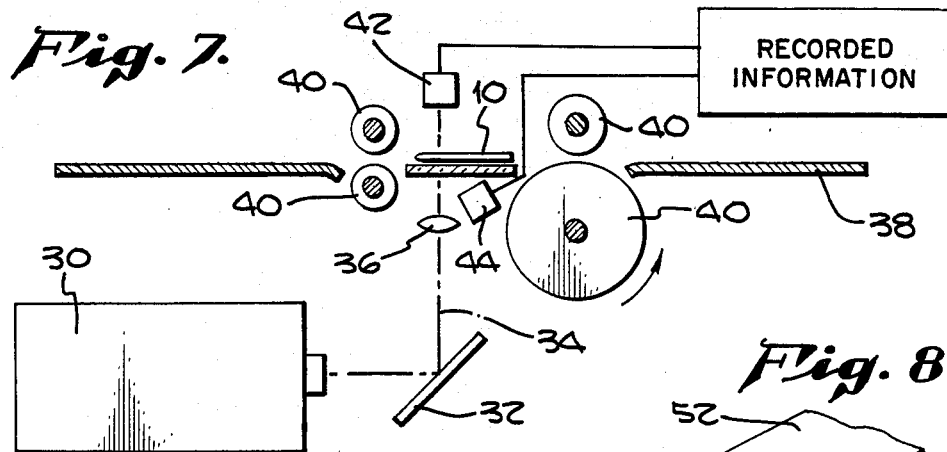
Fig. 7.
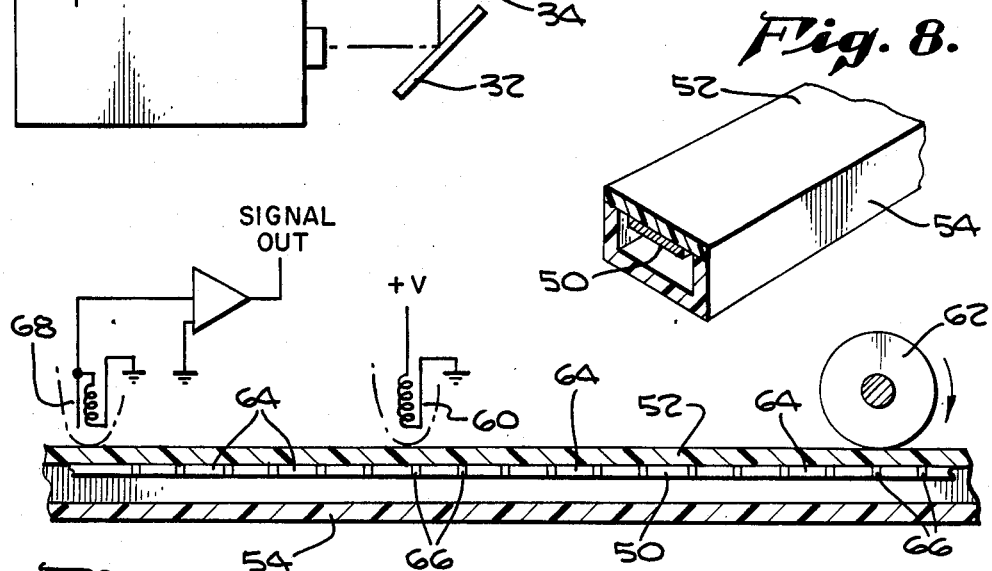
Fig. 8.
Fig. 9.
Fig. 10.

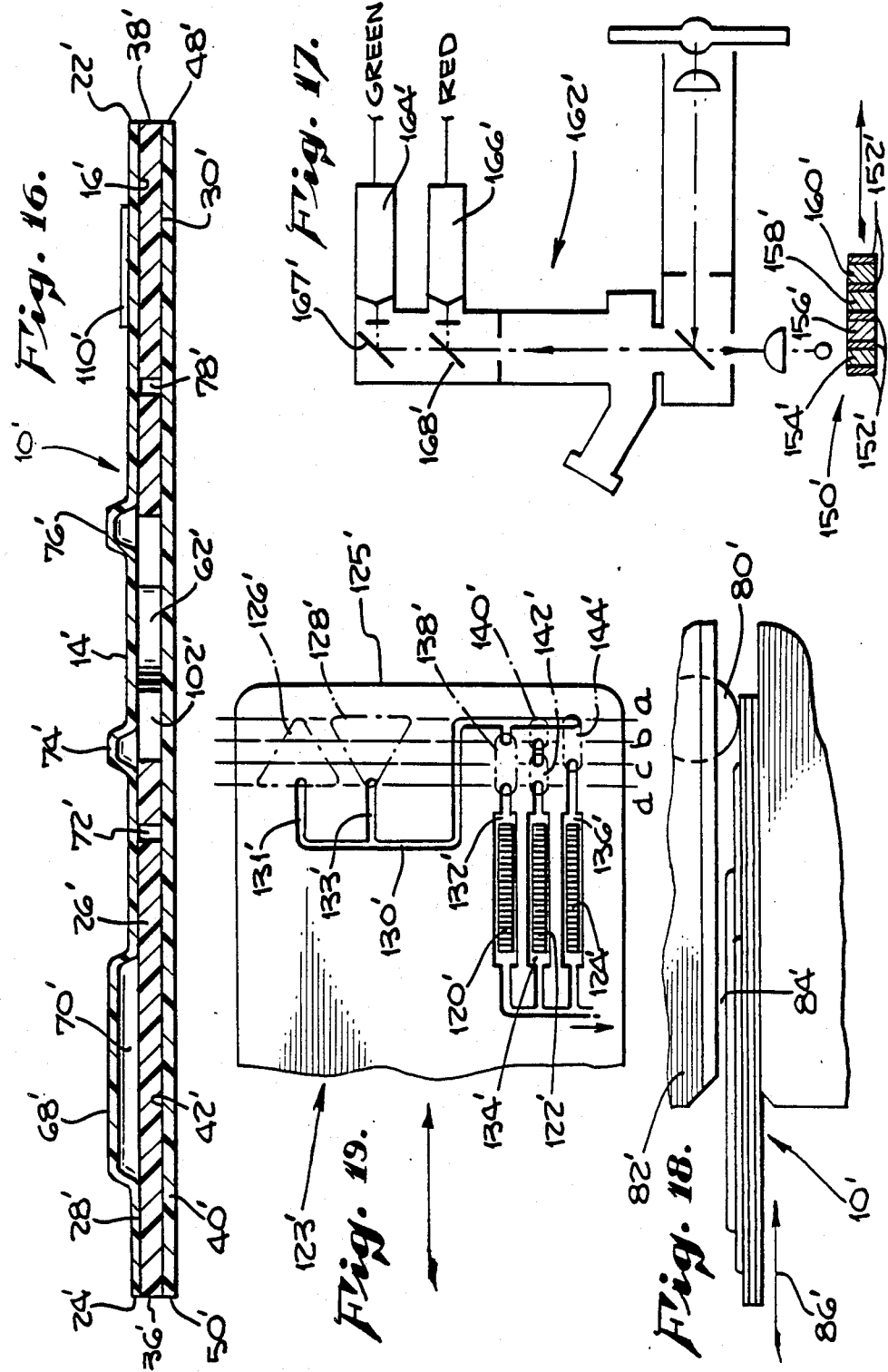

MULTIPLE ASSAY CARD AND SYSTEM

This is a continuation-in-part of my co-pending U.S. patent application Ser. No. 06/526,970 filed 8-26-83, now abandoned.

BACKGROUND OF THE INVENTION

The present invention relates generally to procedures and systems for immunoabsorbent assay. More particularly, the present invention relates to a microassay rod and card system which is capable of testing a single small sample simultaneously for the presence of numerous different biologically important substances.

Immunoassay systems are all based upon the specific yet reversible chemical reactions which occur between an antigen and a corresponding antibody. In general, a known antigen or antibody is absorbed onto or otherwise attached to a solid support. The fixed antigen or antibody is then used to screen or probe various solutions of interest to detect the presence of antibodies or antigens which are immunoreactive with the bound antigen or antibody.

For example, if a test solution is to be screened or probed for a particular antibody, a known antigen which combines specifically with the antibody to be tested for is attached to a suitable support structure. The fixed known antigen is then used to probe a test solution for the presence of the antibody. If the specific antibody is present, it will combine with the fixed antigen to thereby become indirectly bound to the fixed support material. Any unbound antibody and other interfering substances are then removed from the support surface by washing. The presence of any antibody indirectly bound to the fixed support by way of the known antigen is then detected by the use of a second antibody which has a particular characteristic, or includes a suitable marker which can be measured.

Many different types of antibody markers have been developed for use in immunoassay systems. Antibodies tagged with radioisotopes have been popular markers for use in radioimmunoassay; however, the use of radioisotopes requires expensive specialized equipment and specialized handling features. Enzyme Linked Immunoabsorbent Assay (ELISA) is another immunoassay system which has experienced widespread popularity. ELISA is based upon the use of an enzyme linked antibody marker to detect the presence of antibody bound to the fixed antigen. Typically, an enzyme such as horseradish peroxidase is linked to an immunoglobulin which is capable of combining with the antibody being tested. The enzyme is capable of catalyzing an easily measured color producing reaction. The popularity of ELISA type procedures is based in large part upon the ease with which the colored product produced by the enzyme-linked antibody can be detected. In addition to radioisotope and enzyme linked antibody markers, fluorescent compounds, such as fluorescein have been used to provide a fluorescent antibody marker.

With the advent of monoclonal antibodies, and highly specific antigens, it is now possible using immunoassay techniques to probe various test solutions such as blood, sputum or urine specifically and selectively for numerous different immunochemically reactive substances, i.e., those substances capable of engaging in antibody-antigen type reactions. It would be desirable to use these newly available immunochemical probes to provide an assay system in which a large number of specific antibodies or antigens could be screened for simultaneously using a single aliquot of sample and a single test system.

For the most part, the present immunoassay systems utilize a single solid support coated with a single known antigen or antibody. The solid support is then used to probe one or more samples for a single immunoreactive substance (i.e., antigen or antibody). When screening a test solution for more than one antigen or antibody, the test solution must be separated to provide separate aliquots for testing. This type of screening procedure is especially undesirable where a large number of antigens or antibodies are being tested for and where the amount of test solution available is small.

In 1982, Hawkes, et al. published a paper describing a Dot-Immuno-binding Assay (Hawkes, R., Niday, E., and Gordon, J., Analytical Biochemistry 119, 142–147 (1982) which provides for the simultaneous screening of a test solution for a number of antibodies. The Dot-Imnunobinding Assay basically involves dotting a number of different antigens in different places on the surface of a nitrocellulose filter paper. Upon drying, the antigens are bound non-covalently to the paper and remain attached to it during subsequent manipulations. This single piece of filter paper is then used as the solid support to simultaneously test for the presence of antibodies reactive with the dotted antigens. An enzyme-linked antibody and associated chromogenic substrate for the enzyme is then used to "develop" the filter paper to detect the presence of antibodies bound to the dotted antigens on the filter paper.

The Dot-Immunobinding Assay system is well suited for screening a test solution for a relatively small number of antigen or antibodies. Difficulties arise, however, when a large number of antigens or antibodies are to be tested. Such difficulties include problems in spotting a relatively large number of well defined (i.e., non-overlapping) dots of known antigens or antibody on a single filter paper. Problems with reading the closely spaced dots are also expected. If the dots are spaced apart on the filter paper to maintain dot integrity, it is then necessary to use an inordinately large sample of test solution to conduct a simultaneous analysis since a relatively large area of filter paper must be treated with the solution to be tested. Accordingly, there has been a continuing need to provide a multiple immunoassay system which can conveniently, quickly, efficiently and accurately screen a microsized sample for a large number of antigens and/or antibodies.

Although the radioisotope markers, enzyme linked markers and fluorescent markers are all well suited for immuno-absorbent assay of individual antibodies, it would be desirable to provide a new marker or tag which can be used in a multiple immunoassay system to provide accurate and quick identification of a large number of discrete bound antibodies. It would also be desirable to provide a marker whose characteristic can be easily measured and interfaced with computer processing equipment.

It would also be desirable to provide a microassay rod in which a position marker or some other means is provided which allows determination of the absolute position of the microassay rod as it is passed through a reading device. The provision of such markers would facilitate the identification of each probe on the individual rod and insure accurate determinations. In addition, it would be desirable to provide a method in which the detection and measurement of substances of interest which are bound to the various microassay rod probes is maximized.

SUMMARY OF THE INVENTION

In accordance with the present invention procedures and systems are disclosed which provides for the simultaneous testing of a single small sample for the presence of numerous different biologically important substances. The multiple micro assay system in accordance with the present invention can be used to detect and quantify substances which engage in a binding reaction, including the following: Antigen-antibody, nucleic acid hydridization, and receptor-ligand. In general, the system can be used to detect any substance if the material to which it specifically binds can be attached to a solid support. As features of the present invention, a single sample solution can be tested simultaneously for the presence of up to 250 and even more substance, such as antigens or antibodies. The steps involved in the present invention are no more time consuming or cumbersome than for conventional assay of a single substance. The assay system can be read and quantified automatically in less than one second. The system is especially well suited for use with any of the conventional antibody markers, used in immunoabsorbent assays, with the exception of radioactive probes.

One aspect of the present invention is based upon an immunoassay rod which is basically a column of spaced detection layers which are laminated or otherwise bound between alternating spacer layers. Each detection layer includes a known immunoreactive reagent such as a known antigen or known antibody. The immunoassay rod in accordance with the present invention is based upon the same principles as conventional immunoassay systems except that the spaced stacking of the detection layers provides an especially convenient and simple means for simultaneously probing a single solution for a multitude of immunochemically reactive substances. The number of antibodies or antigens which can be simultaneously tested for is quite large. For example, up to 250 and even more antigens or antibodies can be screened for simultaneously by simply preparing an immunoassay rod in accordance with the present invention having the desired number of detection layers.

As a feature of the present invention, the results of an assay carried out using the multiple assay rod can be automatically read by a computer or other suitable device with the evaluation taking no more than one second for all 250 assays. This is a substantial improvement over prior art techniques where test results have to be individually read and recorded. As another feature of the present invention, no more sample or reagents are used during the test for the presence of a large number of different substances than is presently used in prior art procedures for testing the presence of one substance. This feature is especially desirable where expensive reagents are used or where only a small amount of sample is available.

As another aspect of the present invention, a new type of antibody-marker is disclosed which is especially well suited for use with the multiple immunoassay rod system. The new marker in its broadest aspect is a magnetizable marker which can be linked to a suitable antibody for use in detecting the presence of bound antibody or antigens. The use of a magnetizable marker is especially well suited for multiple immunoassay since the magnetizable marker can be detected electrically and input directly into a computer system for data processing and printout.

In accordance with the present invention, a multiple microassay card and system is provided which provides a simple and efficient means for analyzing samples of interest utilizing a microassay rod. No sophisticated machinery is required and the microassay card, by its own geometry and design, provides the programming necessary to control the sequencing and timing of the assay protocol.

One embodiment of the microassay card in accordance with the present invention includes a solid bottom plate, a top plate and a middle plate. The middle plate is sandwiched between the bottom and top plates. A sample slot in the middle plate is provided to receive and hold a microassay rod. The slot may extend completely through the middle plate with the top plate and bottom plate forming the top and bottom surfaces respectively of the chamber in which the microassay rod is located. The top plate includes a flexible portion which extends away from the middle plate to provide a solution chamber in which reagent solutions or other solutions to be used in treating the microassay rod are placed. Conduits are provided between the solution chamber and the microassay rod chamber. As a particular feature of the present invention, a roller bar or other pressure bar is rolled or otherwise passed over the top of the microassay card to squeeze the solution out of the solution chamber and into the microassay rod chamber for interaction and treatment of the microassay rod. If desired, the card can be moved slowly under a pressure bar to achieve the same results.

For more complicated analysis procedures in which one or more reagents are necessary to treat the microassay rod in a number of sequential steps, the microassay card in accordance with the present invention includes various raised channel portions in the top plate which are closed off by the pressure bar or rod as it moves across the card top. The raised channel portions provide a particularly convenient and simple means for programming the additon of reagents, buffer solutions and other liquids at selected intervals and in a selected sequence.

The microassay card, in accordance with the present invention, can be constructed to carry out many of the steps of conventional assays, including aliquoting of a sample, diluting of the sample, titering of a sample, filtering of the sample, washing of the microassay rod, sequential addition of reagents, combining of reagents and rehydrating of lyophilized reagents. All of these various steps may be programmed into the structure of the card without any other changes in the system being required.

As another feature of the present invention, a microassay rod is provided in which fluorescent markers are provided at various points along the microassay rod to provide a means for determining the positon of the microassay rod as it is passed through a reading device. In addition, the use of fluorescent detectors such as fluorscein is provided. The use of fluorescent detectors enhances readability of the microassay probes and lowers detection limits to levels previously not possible when using conventional markers such as horseradish peroxidase.

The above discussed features and attendant advantages of the present invention will become better understood by reference to the following description when considered in conjunction with the accompanying drawings.

BRIEF DESCRIPTION OF THE DRAWINGS

FIG. 7 is a schematic representation of a preferred exemplary system for reading the immunoassay rod.

FIG. 8 is a prospective view of an alternate preferred immunoassay rod shown in position within another preferred support structure.

FIG. 9 is a schematic representation of a reading system designed to detect magnetizable markers when such markers in accordance with the present invention are used to detect the presence of antibodies bound to the various detection layers.

FIG. 10 is a partial perspective view of a preferred manifold and microtiter plate used for testing multiple samples simultaneously.

FIG. 16 is a sectional view of FIG. 2 taken in the III—III plane.

FIG. 17 is an exemplary view of a preferred fluorescent microassay rod as it is being passed by a fluorescent reading device.

FIG. 18 is a side view of the preferred microassay card shown in FIGS. 1–3 being passed through a cassette device having a pressure bar or roller which controls movement of solutions through the microassay card structure, as the microassay card is passed through the cassette.

FIG. 19 is a partial top view of a preferred microassay card in accordance with the present invention which is designed to provide three sample aliquots of differing sample concentration from a single sample.

DETAILED DESCRIPTION OF THE INVENTION

Figure 1:
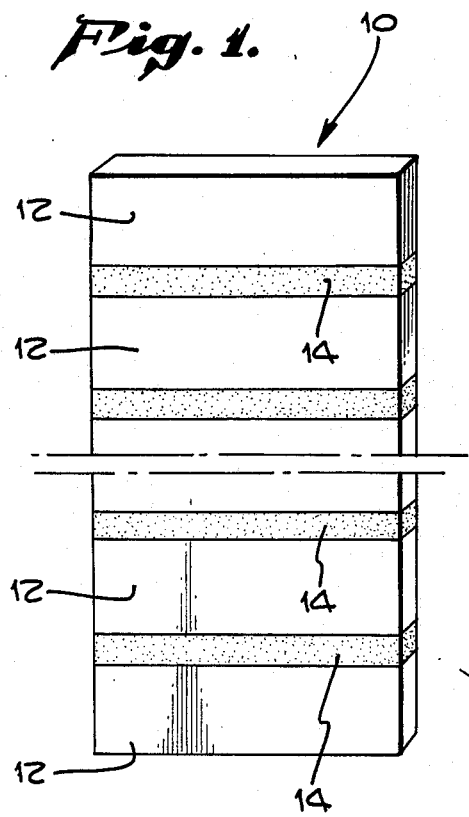
FIG. 1 is an enlarged view of a preferred immunoassay rod in accordance with the present invention.

A preferred exemplary embodiment of a microassay rod in accordance with the present invention is shown generally at 10 in FIG. 1. The rod 10 is basically a column having a plurality of detection layers 12 which are positioned and spaced apart by alternating spacer layers 14. Each detection layer 12 may include one or more reagents which can react with or otherwise provide for the detection of a desired substance. The spacer layers 14 maintain detection layers 12 at spaced location so the immunoassay carried out in each individual detection layer may be discretely measured by a suitable detection system.

The rod 10 in accordance with the present invention has wide application to any type of assay or spot test where a detection reagent is placed on a suitable absorbent for use in detecting the presence of a desired substance. For example, the assay rod can be used for carrying out conventional color spot tests used in qualitative detection of inorganic and/or organic substances. As mentioned above, the multiple microassay system can be used to detect and quantify substances which engage in a binding reaction, including the following: antigen-antibody, nucleic acid hybridization, and receptor-ligand. For example, one use for rod 10 applies the conventional techniques of nucleic acid hydridization to nucleic acids attached to nitrocellulose filters. Single strands of either DNA or RNA can be attached to the solid support and used as a detector layer for complimentary nucleic acid copies. Colorimetric or magnetic methods are then used to detect the hybridization. An additional use incorporates biological receptors onto a solid support for the purpose of detecting the presence of receptor binding substances such as hormones, transmitters, and synthetic ligands.

Although the assay rod in accordance with the present invention has wide application to the detection of substances in general, it is especially well suited for use in immunoassay systems. The following detailed description will be limited to the discussion of preferred exemplary embodiments of the assay rod in connection with immunoassay with it being understood that the present invention has wide application to detection systems not based on immunochemical (antibody-antigen) reactions.

In a preferred embodiment, the assay rod 10 is used for conventional ELISA detection of antibodies or antigens. Each detection layer 12 is preferably made from a suitable absorbent support material which is capable of binding known antigens or antibodies. Typical detection layer materials are nitrocellulose filter paper, plastics, various fibers such as cotton, wool, and numerous synthetic fibers, including nylon, and any other suitable support material which does not prevent immunochemical reactions. Standard nitrocellulose filter paper (e.g. Millipore AA type, pore size from 0.2 to 1.2 microns, or equivalent) is preferred.

The spacer layers 14 can be made from any suitable material which provides separation and positioning of the detection layers 12. It is not necessary that the spacer layers 14 be impervious to water or that it prevent the passage of antigens or antibodies between the various detection layers. It is only required that the spacer layers 14 be inert with respect to antigens and antibodies and that it provide suitable structural positioning and spacing of the detection layers 12. The spacer layers 14 may be made from any of the same materials used for the detection layers 12.

Means must be provided for adhering the spacer layers 14 to the detection layers 12 to provide a laminated rod structure. Any suitable adhesive may be used to stick the detection and spacer layers together. In addition to using adhesives to produce a laminated column of alternating detection and spacer layers, suitable thermoplastic materials may be used as the spacer layers. These thermoplastic materials when heated stick to the detection layers to provide a laminated column of alternating detection and spacer layers.

The preferred assay rod 10 will have a rectangular cross section having a width of between 0.001 inch and 0.005 inch and a length of from 0.010 inch to 0.03 inch. The length of the assay rod will vary depending upon the number of detection layers 12 desired. Rods with up to 250 detection layers are preferred with rods having more than 250 detection layers being possible. Preferably the detection layers will be from 0.002 to 0.006 inch thick with the spacer layers being from 0.001 to 0.005 inch thick.

As previously mentioned, the assay rod in accordance with the present invention may be used for conventional ELISA detection of either antigens or antibodies. The following description of the fabrication of a preferred assay rod will be limited to a rod in which antigens are fixed to the detection layers 12 for use in detecting the presence of antibodies in test solutions.

Standard Millipore AA type nitrocellose filter paper having pores sized from 0.2 to 1.2 microns is cut into one inch squares. For each antibody to be assayed or probed for, its specific antigen is non-covalently absorbed to a single nitrocellulose filter paper square. Preferably, the antigen is in solution and is absorbed onto the filter paper and then dried. Antigens which cannot be bound directly to nitrocellulose filter paper can be covalently linked to chemically derivatized paper which e.g. is commercially available from Schleicher & Schuell and marketed under the name Transbind.

Figure 4:
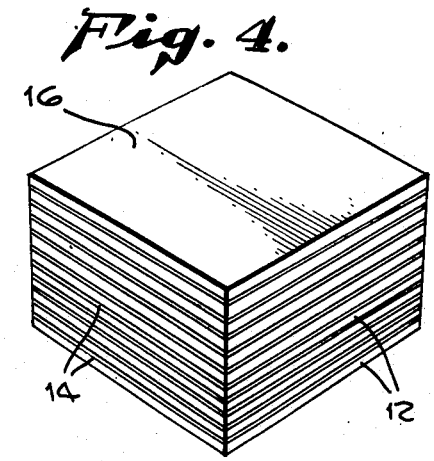
FIG. 4 is a representation of a step in the preferred fabrication of an immunoassay rod in accordance with the present invention.

The filter paper squares (with absorbed antigens) are then stacked with interleaved squares of colored plastic available from Dow Chemical Corp. under the trade name Surlyn 1601. The colored squares of plastic are preferably 0.002 inch thick. The stack of alternating filter paper and plastic layers is compressed and heated to 90 degrees centigrade for 30 minutes. The plastic becomes sticky at this temperature, creating a laminated block of filter papers separated by the opaque colored plastic. If antigens which are inactivated by temperature are being used, a lower melting point plastic such as Suryln 56 can be used. Alternatively, double sided adhesive tape may be substituted for the thermoplastic spacers. The stacking of the alternating filter paper and plastic layers is shown in FIG. 4.

Figure 5:
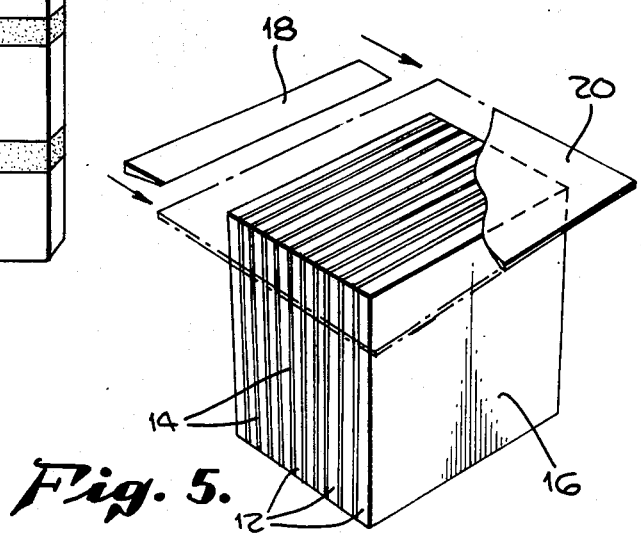
FIG. 5 is a representation of an additional step in fabrication of a preferred immunoassay rod in accordance with the present invention.

As shown in FIG. 5, the laminated block 16 of alternating filter paper and plastic layers is positioned in a microtome with the layers being at a right angle to microtome blade 18. The block 16 is sectioned to produce 0.002 inch sheets of alternating filter paper and plastic layers. Before each cut, an adhesive tape 20 such as Scotch tape, 3M or equivalent is applied to the block face as shown in FIG. 5 to stabilize each section and serve as a backing for the assay rod through subsequent manipulations. Alternatively, a film of clear plastic can be heat sealed to the block face instead of adhesive tape. This step yields approximately 500 pieces of tape to which are attached 0.002 inch thick sheets having lines of alternating antigen impregnated filter paper and plastic layers.

Figure 6:
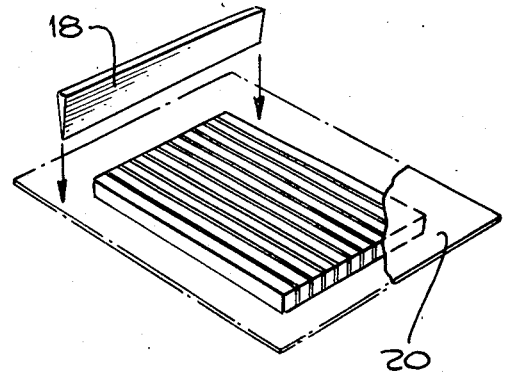
FIG. 6 is a representation of the final preferred cutting step used in preparation of an immunoassay rod in accordance with the present invention.

As shown in FIG. 6, the sectioned sheets with alternating impregnated filter paper and plastic layers are further sectioned into 0.020 inch intervals. The sections are cut at right angles to the lines of filter paper and plastic to thereby produce 50 rods from each section. Thus, the total number of rods which can be produced from the one inch square stack of filter papers is $50 \times 500 = 25,000$. As is apparent, this method of fabricating rods is an especially convenient and quick means for preparing a large number of rods which each are capable of screening for a large number of antibodies.

Figure 2:
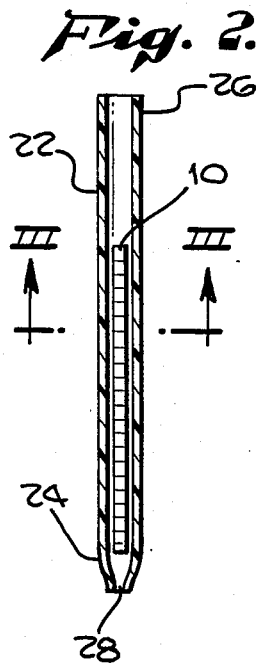
FIG. 2 is a side view of the preferred immunoassay rod inside a support tube.
Figure 3:
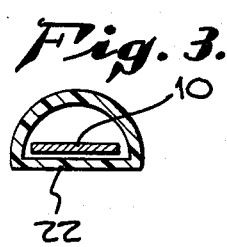
FIG. 3 is a cross-sectional view of FIG. 2 taken in the III—III plane.

The assay rod 10 is preferably placed within a suitable protective structure for use. As shown in FIGS. 2 and 3, the rod 10 is preferably placed within a support tube 22. The support tube 22 may be made from glass, plastic or any suitable structurally strong material which is of optical quality. The tube 22 must be optically clear to prevent any interference with optical reading of the assay rod. The tube 22 has a bottom portion 24 and a top portion 26. The bottom portion 24 includes an opening 28 through which test solution may be drawn for application to the assay rod 10. Preferably, a vacuum apparatus or other suction device is attached to the tube upper support portion 26 to provide the necessary vacuum to draw solution up through opening 28. Other suitable support tubes and channel structures are possible so long as they provide adequate support and protection for the assay rod while not interfering with measurement of the detection layers.

The assay rod with the desired number of detection layers and the various desired known antigens impregnated within the detection layers can be used in any of the conventional ELISA-type test procedures. The following description will be limited to an ELISA-type detection system based upon an enzyme-linked antibody marker. Other ELISA-type detection systems such as the use of a fluorescent antibody marker may be used.

The support tube 22 and enclosed assay rod is attached to a suitable manifold and vacuum is applied to draw up the sample solution above the top of the assay rod 10. The support tube is then incubated for a sufficient time and at a sufficient temperature to allow antibodies within the solution to immunochemically react with their corresponding antigens present in the various detection layers. During incubation, a pulse vacuum source is preferably used to draw the solution up and down in the support tube 26 to assure complete mixing and agitation. After incubation, air pressure is applied to the top 26 of support tube 22 to blow out the test solution. The assay rod 10 is then rinsed a number of times by drawing out and expelling a suitable rinsing solution such as standard saline.

After rinsing, a suitable enzyme-linked second antibody, such as an antibody linked to horse-radish peroxidase (HRP) is drawn up into the tube 22. As is conventionally known, the HRP-linked antibody is chosen such that the HRP-linked antibody will attach to any antibodies which are bound to the detection layers by way of the known impregnated antigens. Typically, if the antibodies being tested for are human antibodies, the enzyme-linked detector antibody or second antibody is preferably an antibody directed against all human IgG antibodies, all human IgE antibodies, all human IgM antibodies or the detector antibody may be directed against all three types.

The detector or marker antibody is incubated at conventionally known temperatures and for conventionally known times followed by washing of the rod to remove any unbound detector antibodies. A color reagent for the HRP-linked antibody, such as diaminobenzidine plus hydrogen peroxide, is then added to the assay rod 10. The colored product produced by any HRP-linked antibody bound to the detection layers is trapped within the respective filter paper layers. The assay rod is then screened using a suitable optical detector to determine which detection layers have colored product. The system herein described can be adapted to the "sandwich assay" for the presence of multiple antigens. Antibodies specific for various antigens are attached to different detector layers and the rod constructed as before. A solution containing many possible antigens to be assayed is then incubated with the rod. Following washing, a solution is added which contains a mixture of marker-labelled antibodies directed against the same antigens as the antibodies attached to the detection layers. The assay is completed and read as before.

FIG. 7 is a schematic representation of a preferred screening system for "reading" the results of the immunoassay carried out using the assay rod. Basically, qualitative and quantitative information can be gained by measuring the amount of colored product found in each filter paper layer. This is done by measuring the attenuation of light passing through an individual filter paper layer as it moves between a light beam and a light detector. As shown in FIG. 7, a light beam is provided by laser 30 by way of mirror 32. The light beam 34 is passed through a suitable lens 36 to provide a beam having a width of 0.002 inches. The tube 10 is positioned on a guide plate 38 and moved past the light beam using a suitable drive wheel system 40. An axially sensor 42 produces an analog signal proportional to the amount of the light beam transmitted through rod 10. A back scatter sensor 44 is provided to register imperfections in the assay rod (principally air bubbles) which might produce artifacts in light transmission. The sensor 44 is also used to test the integrity and uniformity of each rod or channel before it is used in an immunoassay. The signals from sensors 42 and 44 are passed to a computer control unit. The computer control unit also controls the drive wheel assembly so that the signals received from sensors 42 and 44 can be correlated to each individual detector layer to thereby provide accurate measurement and identification of each layer. The system can be designed to provide both qualitative and quantitative information. Other conventional reading systems are of course possible so long as they provide discrete measurement of the transmitted, reflected or fluorescent light of each detector layer. Other optical detection methods, such as phosphorescence, light scattering and polarized light modulation, may also be used.

Another aspect of the present invention, is the use of a magnetizable marker which can be linked to a suitable antibody to provide a particularly desirable marker system for use in "reading" the numerous detector layers present in the preferred assay rods. Instead of tagging a suitable second antibody with an enzyme or fluorescent compound, the second antibody may be tagged with a magnetizable substance such as ferritin. The tagging of antibodies with ferritin and other magnetizable compounds such as colloidal iron, colloidal cobalt or proteinaceous microspheres containing iron oxide particles is well known with numerous magnetizable tags and methods for linking them to suitable antibodies being well known. (See—Ferritin-protein conjugates: Kishida, Y., Olsen, B. R., Berg, R. A. and Prockop, D. J. 1975, J. Cell Biol. 64, 331-339; Colloidal iron: Poynton, C. H., Dicket, K. A., Culbert, S., Frankel, L. S., Jagannath, S., and Reading, C. L. 1983, Mar. 5. The Lancet pg. 524; and Microspheres containing iron oxide: Widder, K. J., Senyei, A. E., and Scarpelli, D. G. 1978. Proc. Soc. Exp. Biol. and Med. 158:141-146.)

Alternatively, magnetic ions can be deposited from a solution by the action of an enzyme conjugated to the second antibody. For example, many companies supply antibodies conjugated with Alkaline phosphatase. The presence of a enzyme can be detected and quantified with a standard histochemical staining procedure, the calcium-cobalt method (see Gomori, G. 1946. Amer. J. Clin. Path. 16, tec. sect. 7,177; or see any manual on enzyme histochemistry, e.g. Pearse, A.G.E., 1968. Histochemistry, Theoretical and Applied, 3rd edition, vol. 1 pp. 495-511, and pp. 710-711). In this reaction, the sites of enzyme activity are assayed by the presence of an organic phosphate ester in the presence of calcium ions, resulting in the deposition of insoluble calcium phosphate. Treatment with soluble cobalt nitrate produces a precipitate of cobalt phosphate, which has a high magnetic susceptibility. The assay rod fabricated for use when magnetizable markers are being used for detection, are basically the same as the previously described assay rods except that the spacing layers are preferably impregnated with iron oxide. Also, it is not necessary that the support tube or tape backing for the rod be of optical quality.

An assay rod for use in a magnetic detection system is shown generally at 50 in FIG. 8. The rod 50 is attached to a cover plate 52 (preferably plastic) which is sealed over a channel 54. Although only a single rod and channel arrangement is shown in FIG. 8, it is preferred that a channel plate (not shown) be used in which a series of parallel channels are formed in a single plate so that numerous rods 50 may be conveniently positioned for multiple sample testing and multiple rod scanning or measurement.

The procedure for screening solutions for particular antibodies is the same for assay rod 50 as for the previously described assay system. The only difference is that instead of using an enzyme-linked antibody to detect the presence of antibody indirectly bound to the detection layers, an antibody linked to a magnetizable marker is used. Instead of a colored product being bound to the detection layers, a magnetizable marker is present.

FIG. 9 is a schematic representation of a magnetic scanner which is used to detect the presence of any magnetizable antibody marker present in the detection layers. The magnetic scanning device is similar to conventional credit card readers. The magnetic scanner includes a stepping motor 62 which controllably passes the channel 54 and enclosed rod 50 past a write head 60. The write head 60 magnetizes any magnetizable marker present in the detection layers 64 of rod 50. The iron oxide present in spacer layers 66 is also magnetized. The rod 50 is then passed by a read head 68. The magnetized iron oxide and any magnetized marker will produce an analog signal from the read head 68 which can be fed directly into a computer for processing. The use of a verticle magnetic medium playback device, in which the 2 poles of the read and write heads are on opposite sides of the M.I. rod, will permit an increased packing density of probes and greater sensitivity than the more conventional system of FIG. 9. The "vertical recording" technique is available from Eastman Kodak or the 3M Company. The use of a magnetizable marker is especially well suited for reading assay rods having a large number of detection layers since it provides a particularly convenient means of direct input into a computer.

As is apparent from the above description, the immunoassay rod in accordance with the present invention provides a particularly convenient means for screening a test solution for a large number of antibodies using conventional techniques which were previously limited to simultaneous detection of only a few antibodies.

Instead of using filter paper detection layers and interleaved plastic layers, an alternative assay rod in accordance with the present invention can be fabricated from various threads such as nitrocellulose thread or other suitable thread such as nylon, cotton or the like. In general, the assay rod is fabricated by first treating the desired number of threads with the desired number of known antigens to provide antigen impregnated threads. The antigen impregnated threads are then aligned in parallel and stretched tight using a loom. A piece of adhesive tape or other backing material is then attached to the parallel threads. The tape may then be sectioned in a manner similar to the procedure previously shown in FIG. 6. Spacer threads of different color which are not impregnated with antigens may be placed in between the antigen impregnated threads if desired to provide easier identification and positive spacing of the antigen impregnated threads. In addition, the detection layers for the assay rods in accordance with the present invention may be produced by printing the known antigens in thin lines onto filter paper. Filter paper may then be cut into thin rods with the rods being applied to a suitable adhesive backing in a manner similar to the procedure used for antigen impregnated threads.

Figure 11:
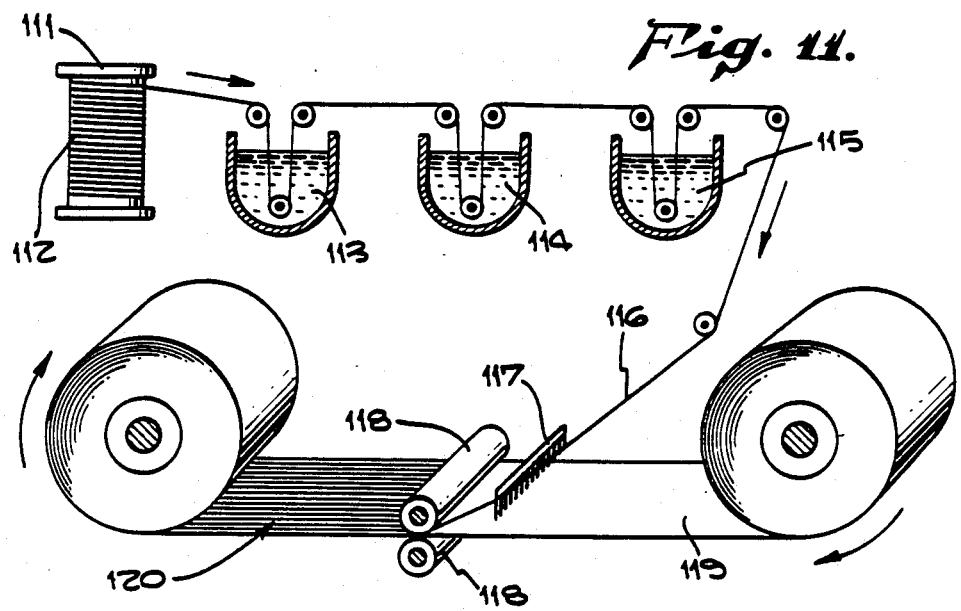
FIG. 11 is a diagram showing the exemplary processing method for making rods in accordance with the present invention.

A method of fabrication of nylon monofilament threads coated with antigens or antibodies, which can be incorporated into an exemplary microassay rod is shown in FIG. 11. Depending upon the number of probes desired, one or more bobbins 111 containing nylon monofilament line 112 are set up. For simplicity, only one bobbin and monofilament nylon line are shown in FIG. 11. The thread 112 is first treated chemically by slowly pulling the thread 112 through a sensitizing solution 113 containing a bifunctional reactive substance which covalently attaches to the nylon surface. The filament 112 is then slowly pulled through the antigen or antibody solution 114 which reacts covalently with the other half of each bifunctional reactive substance. The filament 112 is then finally passed through a wash bath 115 where a wash solution is provided to react with any remaining reactive substances on the nylon.

The chemistry of attaching proteins to nylon threads has been worked out (Sundaram, P. V. and Hornby, W. E. 1970. FEBS Lett. 10:325-327, and Sundaram, P. V. 1977, in Biomedical Applications of immobilized enzymes and proteins. Thang, T. M. S. ed. pp. 317-340. Plenum Press, New York.). Gordon, N. C., Shihita, M.; and Hall, P. F. 1974. J. Ultrastruct. Res. 47:285-295.

Alternatively, the immunoreagent can, using a similar process, be attached by non-covalent adsorption to a thread made from a suitable polymer. (Catt, K. and Tregear, G. W. 1967. Science 158:1570-1572.)

The treated thread 116 is then pulled through a weaving comb 117 which aligns each thread in parallel. The thread 116 is then pressed by suitable rollers 118 or other device onto adhesive tape 119. The tape 119 with thread 116, plus other desired threads shown generally at 120 may then be sectioned in a manner similar to the procedure previously shown in FIG. 6.

When numerous samples are to be tested simultaneously, the immunoassay rods and support tubes may be arranged in a manifold as shown in FIG. 10. The manifold shown generally at 70 includes an upper manifold plate 72 which has a central vacuum attachment 74 which can be connected to a vacuum system to draw samples up into the support tubes 76. The manifold can be positioned over a standard microtiter tray as shown at 78 for the simultaneous analysis of numerous different samples present in the individual wells 80 in microtiter tray 78. Washing and subsequent treatment steps are carried out by placing the manifold 70 over additional microtiter plates having the desired wash solution or marker antibody etc. in the microtiter plate wells.

Figure 12:
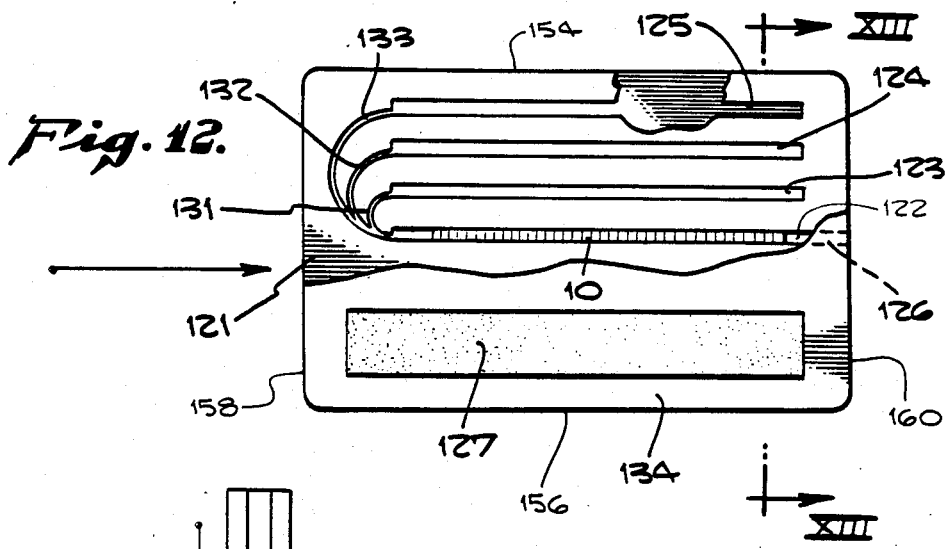
FIG. 12 is a top view of a preferred microassay card.
Figure 13:
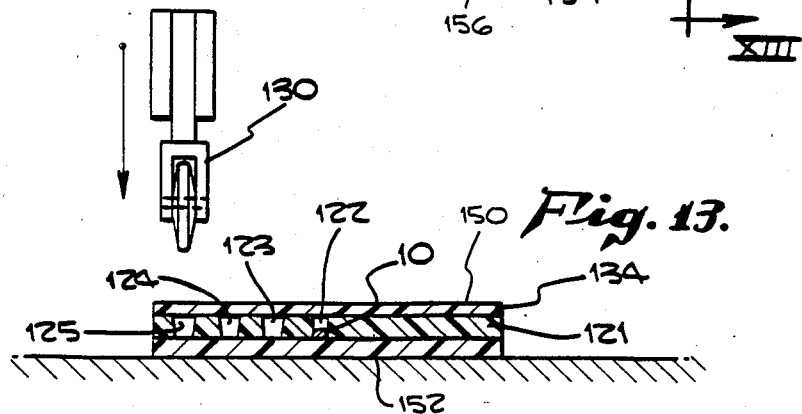
FIG. 13 is a side view of a preferred microassay card.

An example of an assay system based upon the microassay rod 10 in accordance with the present invention is shown in FIGS. 12 and 13. Card 121 includes top 150, bottom 152, sides 154 and 156, first end 158 and second end 160. Referring to FIG. 12, a plastic card 121 is provided which has a series of closed channels 122, 123, 124 and 125. The microassay rod 10 is positioned in channel 122. Channel 122 defines a reaction zone for housing the microassay rod wherein reaction of the microassay rod with various reagents takes place. Channels 123, 124 and 125 define treatment solution reservoirs for containing treatment solutions such as, reagents and wash solutions. The sample to be tested is inserted into channel 122 through opening 126 or by other suitable injection. The card 121 includes a magnetic or optically coded information strip of the type conventionally used on credit cards which contains all of the information pertaining to the desired assay and analysis of results. After loading of the sample into channel 122, the card is fed into a card reading device, which reads the magnetically or optically coded information on strip 127 which identifies, among other things, the probes on the rod, the method of their assay, the previously calibrated data for each probe and information on the analysis of the quantitative results. The card is then incubated according to information read from strip 127 for the desired incubation time. The card is then passed under a solenoid operated roller 130 which squeezes the test sample out of channel 122 through opening 126. The card is then moved automatically so that channel 123 is placed under solenoid actuated roller 130. The roller 130 is then used to force wash solution from channel 123 through conduit 131 into channel 122. After a suitable time period, the wash solution may then be removed from channel 122 by way of the solenoid operated roller 130. Then, the card is then positioned so that channel 124 is placed under roller 130. The card and/or roller 130 are then moved so that the desired chromagenic second antibody or other detecting solution is forced from channel 124 through column 132 into channel 122. After a sufficient time to allow the chromogenic second antibody to react with the rod 10, the chromogenic solution is removed from channel 122 by roller 130. Wash solution in channel 125 is then forced into channel 122 by roller 130 which forces this solution through conduit 133 and into contact with rod 10. Although the card is shown utilizing only four channels, it is possible to utilize as many channels as desirable or necessary to provide the desired analysis. The cover layer 134 for card 121 (see FIG. 13) is preferably made from a suitably flexible material which can be deformed by roller 130 so that the various solutions in channels 122-125 can be moved by the peristaltic action induced by roller 130. The roller 130 provides means for selectively transferring reagent, sample and wash solutions by peristaltic action into and out of the reaction zone defined by channel 122. Also, more than one solenoid operated roller may be used if desired.

Examples of practice are as follows:

An assay rod having nine detection layers was prepared as described above from filter paper and Surlyn plastic. The rod was approximately 100 microns thick, 0.5 mm wide and 4 mm long. The rod was mounted within a round glass pipette, 13 cm long, 50 microliter volume. The rod was used to detect the presence of a purified mouse monoclonal antibody directed against human Chorionic Gonadotrophin. A 100 microliter test solution containing 10 nanograms/ml was tested. The nine detection layers or probes were either untreated (blanks) or contained approximately 100 ng of various mixed or purified proteins. The order of detection layers in the rod was: Blank, human transferrin, bovine serum albumin, human Chorionic Gonadotrophin antigen, fetal calf serum, luteinizing hormone, blank, blank, blank. Following incubation with the test solution containing the Chorionic Gonadotrophin antibody, its binding was detected essentially by following the procedures of a Vectastain kit (available from Vector Laboratories, Inc.), containing a biotinilated second antibody directed against mouse IgG heavy and light chains. A horse radish peroxidase color development reagent (BioRad Laboratories) was used. The only detection layer which showed a positive stain was the layer containing the human Chorionic Gonadotrophin.

A second rod having 79 detection layers and a length of 18 mm was prepared as set forth in the first example. The detection layers contained protein extracts from various parts of the brain and other tissues of rat, mouse, chicken and human origin. The above rod was used to detect and characterize monoclonal antibodies present in the supernatants of hybridoma cultures. This assay detected various monoclonal antibodies with differing specificities determined by the MI rod assay correlated with results obtained by binding the monoclonal antibodies directly to tissue slices, using conventional immunohistological techniques.

As is apparent from the preceding description, the assay rod of the present invention is a valuable new analytical tool for conducting a large number of tests simultaneously on a small sample. In an addition to the above described features and advantages, a single assay rod can use some of its detector layers as internal standards, internal positive controls, and internal negative controls. This greatly aids in quantitation, and in detecting false negatives and false positives. For example, these controls would be as follows:

a. Internal standard: if the second antibody had an enzyme marker, then a known amount of that enzyme could also be incorporated into one of the detection layers. The color development in this layer would be a standard used to quantitate the amount of enzyme present in the other layers.

b. Internal positive controls. For example, the unlabeled second antibody could be incorporated into a detection layer. Then, if any first antibody was in the test solution, and the assay was working properly, this layer should stain.

c. Internal negative controls. Layers containing substances to which antibodies should not bind. If these layers stained during the assay, then something is amiss.

Further advantages include the fact that different concentrations of the same antigen can be applied to different layers, providing an internal dose-response curve. In addition, the microassay rod serves as a small and conveniently stored permanent record of the test results.

The microassay system is easily adapted to the detection of nucleic acid hybridization (in fact nitrocellulos filters first gained general use for this purpose). There are now a multitude of cloned genes to be used as probes so that the microassay system has great utility in human genetic screening and in the identification and typing of microorganisms by the hybridization of their genetic material, to mention only two applications. In addition, there are a number of other molecular interactions between two substances which can be exploited to test for the presence of one or the other substances such as:

| Molecule | To test for |
| --- | --- |
| 1. Receptor | Hormone, transmitter, synthetic ligand, drug |
| 2. Lectin | Sugars or polysaccharides |
| 3. Enzyme | Substrates or cofactors. |

Figure 14:
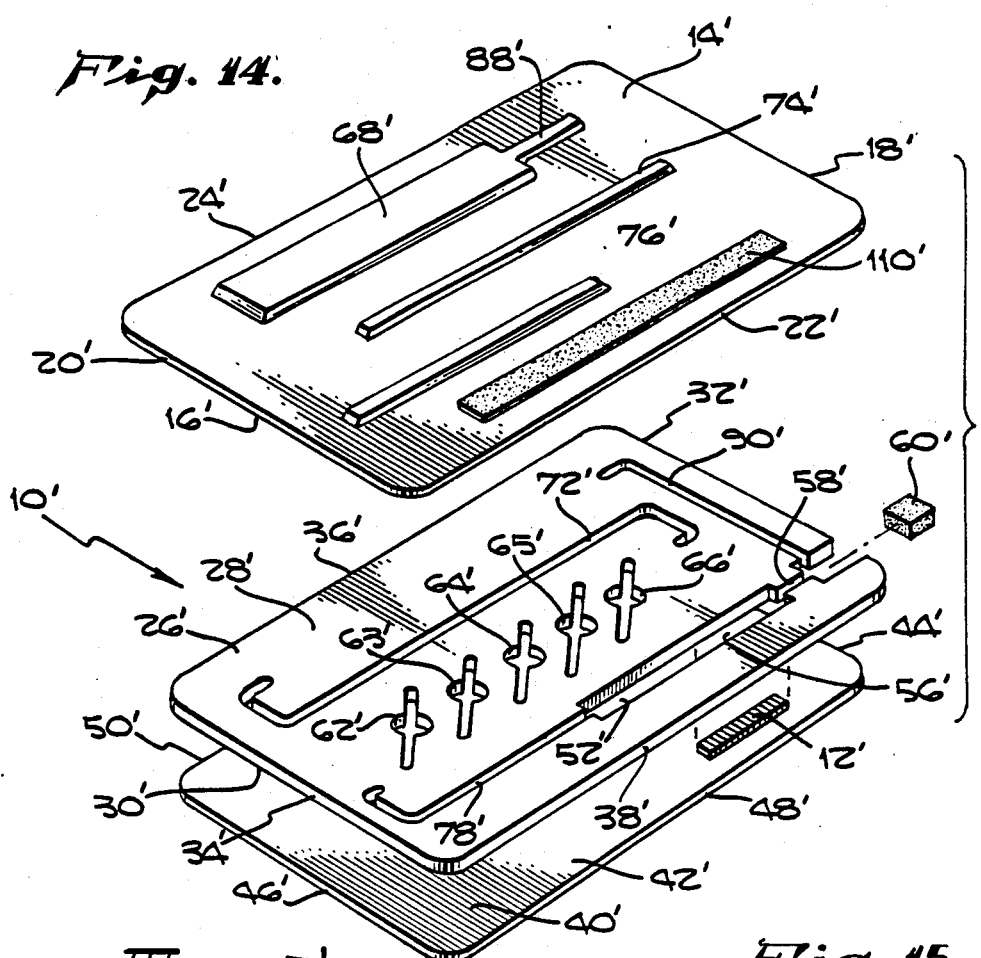
FIG. 14 is an exploded perspective view of a second preferred microassay card in accordance with the present invention showing the bottom plate, middle plate and top plate.
Figure 15:
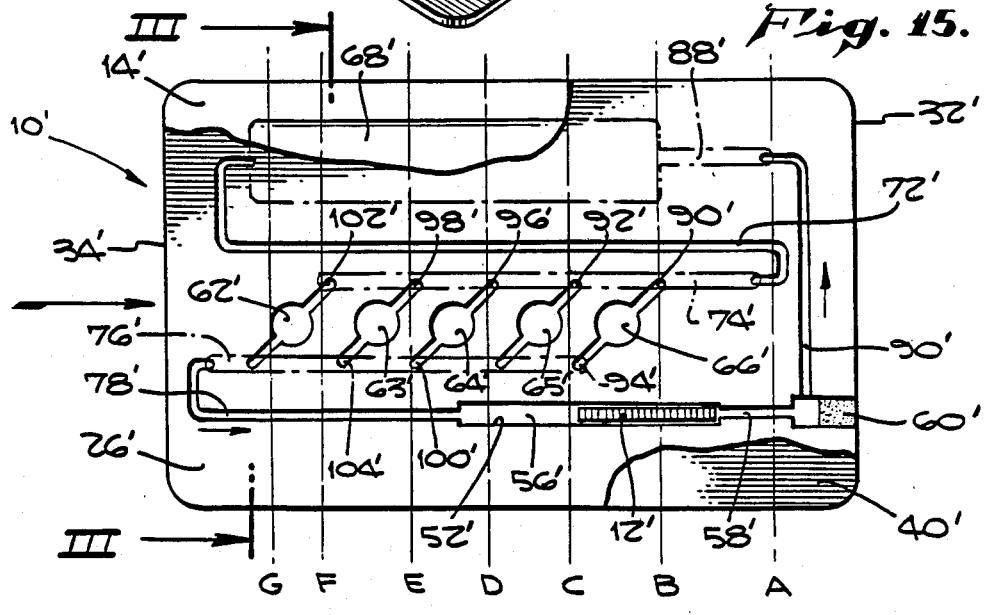
FIG. 15 is a top view of the preferred microassay card shown in FIG. 1.

A preferred microassay card in accordance with the present invention is shown generally as 10' in FIGS. 14-16. The microassay card 10' is designed to house a microassay rod 12' which is to be treated with sample and reagents to carry out immunochemical or other assays. The microassay card 10' is similar to the card based assay system shown in FIGS. 12 and 13, except that the card is modified as will be described in detail to allow programmable control of fluids which are passed into contact with the microassay rod 12' as the card 10' is passed under a pressure bar or wringer which extends laterally across the top of the microassay card 10'.

The microassay card 10' includes a top plate 14' having a bottom surface 16', front end 18', rear end 20', and sides 22' and 24' extending between the front end 18 and rear end 20'. The card 10' also includes a middle plate 26' which has a top surface 28', bottom surface 30', front end 32', rear end 34' and sides 36' and 38' extending between the front end 32' and rear end 34'. A solid bottom plate 40' is provided which has a top surface 42', front end 44', rear end 46' and sides 48' and 50' extending betweem the front end 44' and rear end 46'. The plates 14', 26' and 40' are preferably made from a suitable plastic material. However, any suitable material can be utilized, such as glass or composite materials, so long as a rigid, inert card structure is provided which has the desired flexible characteristics as will be discussed below.

The middle plate 26' is sandwiched between the top plate 14' and solid bottom plate 40' to provide a laminated card which is preferably approximately the size of a conventional credit card or smaller. Other card sizes are, of course, possible, depending upon the particular assay being carried out. The plates may be laminated together by any convenient means including heat bonding or cementing with various adhesives.

As best shown in FIGS. 14 and 15, the middle plate 26' is provided with a sample slot 52' which is adapted to receive and hold a microassay rod 12'. The slot 52' extends from the middle plate top surface 28' to the middle plate bottom surface 30' and when sandwiched between the top plate 14' and bottom plate 40' defines a microassay rod chamber 56'. An inlet 58' into the microassay rod chamber 56' is provided so that sample solutions to be tested may be introduced into the rod chamber 56' for analysis. Removable plug 60' is provided for sealing inlet 58' once the sample has been introduced. The card 10' may be fabricated with the microassay rod 12' in place or the microassay rod 12' may be inserted into the rod chamber 56' through inlet 58' after the card has been fabricated. In a preferred embodiment, plug 60' is fixed in place and a syringe is used to inject the sample through plug 60'. In this situation, plug 60' is preferably made from a resilient material to facilitate puncturing by the injection syringe.

The microassay card 10' shown in FIGS. 14–16 is designed for use in an analysis where five different reagents or treating solutions are to be transferred to rod chamber 56' for treatment of the microassay rod 12'. Reagent slots or chambers 62', 63', 64', 65' and 66' are provided in middle plate 26'. Various reagents and substrates which are to be sequentially fed to the rod chamber 56' are contained within the reagent chambers 62', 63', 64', 65' and 66'. These reagents may be either liquid or powder. In this preferred embodiment, the reagents in reagent chambers 62', 63', 64', 65' and 66' are sequentially swept or transported to the rod chamber 56' by a buffer or other solution designed for that purpose as described below.

The top plate 14' includes a flexible indentation 68' which extends away from the middle plate and defines a buffer or solution chamber 70' (FIG. 16) in which the buffer or other transporting solution is housed. The solution in chamber 70' is transported to the rod chamber 56' through conduits 72', 74', 76' and 78'. The solution in chamber 70' is passed sequentially through reagent chambers 66', 65', 64', 63' and 62' by way of the unique valving action provided by the conduits 74' and 76'. Both of these conduits are flexible indentations in the top plate 14' which extend away from the middle plate 26' to provide a flexible channel between the top plate and middle plate. By applying localized pressure at various points along the flexible conduit 74' and 76', flow of solution through the conduits can be controlled.

The solution in chamber 70' is pressurized and forced through the various conduits and reagent chambers by a roller or other pressure device 80' (See FIG. 18). Preferably the roller bar or pressure bar 80' will be housed within a cassette or other housing device 82' which has an opening 84' into which the microassay card 10' can be fed in the direction shown by arrow 86'. The roller 80' is positioned so that it extends laterally across the card as represented by phantom lines A–G in FIG. 15. The roller is positioned so that it deforms or presses the indentations 68', 74' and 76' against the middle plate 26'. This rolling or wringing action of roller 80' squeezes solution out of solution chamber 70' into conduit 72'. The flow of the solution from chamber 70' through the various reagent chambers 62', 63', 64', 65' and 66' is controlled by the pressure bar 80' as it passes over the indented channels 74' and 76'.

Referring to FIG. 15, the position of the roller or pressure bar 80' is shown at various positions A–G as the microassay card 10' is moved through cassette 82'. In position A, the roller bar is positioned over indented channel 88' only. In this position, sample can be loaded into rod chamber 56' without the possibility of sample solution flowing through conduit 90' and into solution chamber 70'. The positioning of roller bar 80' over conduit 88' acts as a valve mechanism to close off any flow of fluid through channel 90' and channel 88'.

As the pressure bar 80' moves to position B, the bar begins to compress the forward edge of solution chamber 70' to begin forcing solution through channel 72'.

The roller bar 80' at position B is positioned just past the point 90' where flexible channel 74' is connected to reagent chamber or slot 66'. Since flexible channel 74' is pinched closed just past point 90', the solution from chamber 70' is forced through reagent slot 66' and into flexible channel 76', conduit 78' in middle plate 26' and into the rod chamber 56' for contact with microassay rod 12'. The solution and reagent exiting from chamber 56' are passed through channel 90' and back through flexible channel 88' into the solution chamber 70' at a position behind the pressure bar 80'. Since pressure bar 80' is no longer positioned over flexible channel 88', solution is free to flow through channels 90' and 88' into the solution chamber 70'. This provides an especially convenient means for containing waste reagent and solution within the card system to provide a completely self-contained analytical unit. The flexible channel 88' and indentation 68' both function as pressure valves. As the bar 80' moves across both spaces, it pushes fluid before it thereby making room for fluid to fill the space behind it.

As the roller bar 80' is moved to position C, solution from chamber 70' is continually forced through conduit or channel 72', through reagent chamber 66', flexible channel 76', conduit 78' and rod chamber 56'. At position C, the bar 80' is located just past the point 92' where the reagent slot or chamber 65' is connected to flexible channel 74'. Since the bar 80' is located just past point 92', solution from chamber 70' is now forced through reagent chamber 65'. Additionally, the bar 80' at position C is located at point 94' on flexible conduit 76' to prevent flow of solution through reagent slot 66'. As the bar 80' continues to move towards position D, the solution from chamber 70' is continually forced through reagent chamber 65'.

At position D, the bar 80' is now located just past the point 96' where the reagent chamber 64' is connected to flexible channel 74'. This allows the solution from chamber 70' to be forced through reagent chamber 64' and to sweep the reagent or other contents of chamber 64' into flexible channel 76', channel 78' and rod chamber 56'. The roller bar 80' in position D closes off flexible channel 76' so that solution from chamber 70' no longer can flow through reagent chamber 65' or 66'. As the pressure bar 80' continues to move to position E, solution from chamber 70' is continually forced through reagent chamber 64' and into rod chamber 56' via conduits 76' and 78'.

At position E, the pressure bar or roller 80' is located just past the point 98' where reagent chamber 63' connects to flexible conduit 74'. The location of pressure bar 80' at position E allows the solution in chamber 70' to be forced through reagent chamber 63'. As in the prior sequences, the pressure bar at position E is located just past the point 100' at which the reagent chamber 64' joins flexible conduit 76' to thereby prevent the flow of solution through reagent chambers 64', 65' and 66'. Again, as the pressure bar continually moves across the card 10' towards position F, solution from chamber 70' is continually passed through reagent chamber 63' and into the rod chamber 56'.

When the rod 80' reaches position F, it is located just past point 102' where reagent chamber 62' is connected to flexible channel 74'. The location of pressure bar 80' at position F allows the solution in chamber 70' to be passed through reagent slot or chamber 62'. Likewise, the pressure bar 80' at position F is located just past the point 104 where the reagent chamber 63' joins flexible channel 76' to thereby cut off flow of solution through reagent chambers 63', 64', 65' and 66'. Solution from chamber 70' is continually forced through reagent slot 62' as the pressure bar is moved toward position G.

The number of reagent slots or chambers may be varied from one to any desired number with five reagent chambers being shown as an exemplary embodiment. The size and shape of the reagent chambers may be varied depending upon the amounts and types of reagents to be added. The reagent chambers should be designed so that the inlets and outlets to the reagent chambers which are connected to the flexible conduits 74' and 76' in the top plate 14' are arranged as shown in FIG. 15 so that the movement of roller bar 80' across the card provides a desired selective transfer of solution through the individual reagent chambers.

Many times when treating a microassay rod with numerous different reagents, it is desirable to incubate the rod, rinse the rod between reagent treatments and other process steps. The cassette 82' can be provided with heating elements for incubation and the card 10' may be provided with additional solution chambers 70' located at positions on the card to provide introduction of various solutions into the rod chamber 56' at varying times during analysis depending upon the relative location of the solution chambers on the card. Many times it is desirable to program passage of the card through the cassette so that the roller 80' remains stationary relative to the card for given times. A convenient means for providing program information is a coated magnetic information strip 110'. This information strip is coated much like magnetic coating strips for conventional credit cards to provide suitable information to the central electronic control unit for the cassette which controls the speed at which the card 10' is processed or passed under roller bar 80'. It is preferred that a single system be provided to process the card and to move the various chemicals through the channels into contact with the microassay rod. A second system is then provided for reading the results of the assay. If desired, these two systems can be combined into a single unit where the microassay card is automatically passed from the processing section (see FIG. 18) to the reading or analysis section (see FIG. 17).

Many times it is desirable to analyze a particular sample or substance at different sample concentrations or sample strengths. In general, the concentrated or pure sample will be tested and then various serial dilutions of the sample will be made with a suitable buffer or diluent. Tests on the undiluted sample and various diluted samples will then be made.

As shown in FIG. 19, a system is provided in accordance with the present invention wherein a single sample may be diluted with buffer or diluent to produce samples of varying concentrations which are introduced or absorbed onto individual microassay rods. The exemplary embodiment shown in FIG. 19 covers a situation where three different sample concentrations are applied to three different microassay rods 120', 122' and 124'. The microassay card with the sample dilution configuration shown in FIG. 19 is based upon the same concept as the microassay card shown in FIGS. 14–16 wherein the solution to be transported through the card is placed in a flexible indented portion in the top plate which is subsequently deformed by a roller or pressure bar to force the liquid through various conduits and channels in the top plate and middle plate.

The sample dilution system shown in FIG. 19 includes a flexible sample solution chamber 126' in the microassay card shown generally at 123'. The sample solution chamber 126' tapers outward as you move from the front end 125' of the card to the rear end 127' of the card 123'. A flexible buffer chamber 128' is provided in which suitable buffer or diluent is stored. The buffer chamber 128' tapers inward as you move from the front end 125' of the card to the rear end 127' of the card. Both chambers 126' and 128' have outlets 131' and 133' connecting to a conduit 130' in the middle plate of the card. Rod chambers 132', 134' and 136' are provided for housing three microassay rods 120', 122' and 124', respectively. The conduit 130' leading from sample chamber 126' and buffer chamber 128' is connected to rod chamber 132' via flexible conduit 138' located in the card top plate. The conduit 130' is connected to the second rod chamber 134' via flexible conduits 140' and 142', while the third rod chamber is connected to channel 130' through flexible conduit 144'. When the roller bar 80' is in position "a" as shown in FIG. 19, it is located adjacent to the sample and buffer chambers 126' and 128'. As the roller bar 80' is moved to position "b", buffer and sample are forced through channel 130' and flexible conduit 138' into chamber 132'. The roller bar during this time is positioned over flexible conduits 140' and 144' to thereby prevent flow of sample and buffer into rod chambers 134' and 136'. The relative shapes of the sample and buffer chambers 126' and 128' are such that the sample in chamber 126' is diluted with a relatively large amount of buffer from chamber 128'.

As can be seen, as the roller bar 80' moves from position "a" to position "d", the amount of buffer or diluent being forced through channel 130' decreases while the amount of sample solution increases. The concentration of sample in the solution being introduced into chamber 132' is therefore relatively low. As the bar 80' moves to position "b", the bar pinches off the flexible conduit portion 138' to cut off flow of solution into chamber 132'. At the same time, the bar 80' moves past flexible conduit 140' to thereby allow flow of solution into chamber 134'. The roller bar in position "b" remains at a location which pinches flexible conduit 144' closed to prevent flow of solution into chamber 136'. As the bar travels from position "b" to position "c", sample diluted with a lesser amount of buffer is passed into chamber 134'.

When the pressure bar 80' reaches position "c", the bar contacts flexible conduit 142' to thereby pinch the conduit closed and cut off flow of solution to chamber 134'. The bar in position "c" remains on flexible conduit 138' to continue to prevent solution from passiong into chamber 132'. At position "c", the bar is located just past flexible conduit 144' to thereby allow solution to flow from conduit 130' into chamber 136'. Between positions "c" and "d", the relative amount of buffer being introduced into conduit 130' is much less than the amount of sample being passed therethrough to thereby provide a solution having a high sample concentration as compared to the sample concentration of the solutions passed into chambers 134' and 132'.

The sample dilution system shown in FIG. 19 may be used alone or in combination with the reagent addition system shown in the microassay card 10' shown in FIGS. 14–16.

In FIG. 17, a portion of an exemplary microassay rod for use with fluorescent marker systems is shown generally at 150'. The microassay rod 150' includes spacer layers 152' and probe layers 154', 156', 158' and 160'. The spacer layers 152' and probe layers 154'–160' are made from the same materials as described previously and fabricated into a microassay rod in the same manner as previously described.

In accordance with an aspect of the present invention, probe layers 154' and 158' are impregnated with cresyl violet or any other suitable fluorescent marker such as rhodamine. The cresyl violet impregnated probes 154' and 158' provide a convenient means for determining the position of the rod 150' as it is passed by a detection device such as the epifluorescence microscope shown generally at 162' in FIG. 17. The rod 150' is illuminated by means of a DC mercury arc and the standard FITC filter cube of the epifluorescence microscope. The rod is thereby illuminated with blue light at wavelengths of 450 to 480 nanometers. Fluorescence emitted from the cresyl violet stained probes 154' and 158' has a wavelength of approximately 630 nanometers. This fluorescence is passed into the epifluorescence microscope and detected by photomultiplier tube 164'. The two other probes 156' and 160' are detection layers which are impregnated with various known antigens or other specific binding reagents as previously described. The antigen or reagents in probes 156' and 160' are designed to selectively react with particular substances in a sample. When using the cresyl violet marked assay rod 150' and fluorescent microscope 162', it is desirable to use fluorescent detectors such as antibody markers conjugated with fluorescein or other suitable fluorescent materials such as phycoerythrin (Becton-Dickinson). Fluorescein is a particularly preferred marker for use in detecting the presence of absorbed compounds on the probes 156' and 160'. Fluorescein when radiated with blue light (450 to 480 nanometers) emits fluorescence having a wavelength of approximately 520 nanometers. The fluorescence emitted from the probe layers 156' and 160' enters the epifluorescence microscope as the rod 150' is passed by the microscope objective and is measured by a second photomultiplier 166'. The dichroic mirrors 167' and 168' separate the fluorescent light into red and green components, which go, respectively, to photomultiplier tubes 164' and 166'. The housing which contains the two photomultiplier tubes and the two dichroic mirrors is not found on the standard epifluorescence microscope.

Since the cresyl violet impregnated probe layers 154' and 158' emit fluorescence at a different wavelength than fluorescein, the various cresyl violet impregnated layers and those detection layers or sample layers in which fluorescein is present can be distinguished from each other. By placing the cresyl violet impregnated probe layers at various positions throughout the microassay rod 150', it is possible to determine the exact position of the microassay rod and the particular sample probe layer 156' or 158' which is being measured. As will be realized, only a small portion of a typical microassay rod is shown at 150' in FIG. 17. In general, the microassay rod will include a large number of probe or detection layers. The positioning of cresyl violet impregnated marker layers at pre-determined positions in a pre-determined sequence allows one to determine accurately the absolute position of the microassay rod as it is moved past the epifluorescence microscope 162' for measurement of individual layers. The use of fluorescein marked antibodies and other fluorescently marked detection substances to detect the presence of reactive materials on the various detection layers is preferred since the sensitivity of measurements can be increased over the limits available using conventional horseradish peroxidase or other conventional markers.

A certain amount of scattered light is produced when the microassay rod is illuminated. The scattered light is blue light which is reflected back from the rod. It is low when a spacer is under the light beam and high when a probe is under the light beam (that is when nylon or nitrocellulose filters are used for probe material and observed in an aqueous or air environment). Thus the scattered light can be used to tell when an individual probe has entered the field of the light beam. This is important not only for locating each probe, but for setting the limits for integrating the fluorescence light output over the entire probe as it passes the light beam. Integration will increase sensitivity and decrease noise.

Another way of increasing the sensitivity of the system is to contain the scattered light within the probe until it has a chance to interact with a fluorescent molecule. This is accomplished by making the spacers out of reflecting material and using reflecting backing tape. Each probe then becomes a kind of light pipe. This becomes increasingly important as the size of the probe is decreased (particularly as the thickness is decreased). Thus as one goes to higher linear densities of probes, the importance of using reflecting spaces and backing material increases.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is limited only by the following claims.

What is claimed is:

1. An assay card adapted for treating and analyzing a sample comprising:

a solid bottom plate having a top surface, a front end, a rear end and sides extending between said front and rear ends;

a top plate having a bottom surface, a front end, a rear end and sides extending between said front and rear ends;

a middle plate having a top surface, a bottom surface, a front end, a rear end and sides extending between said front and rear ends, said middle plate being sandwiched between said bottom and top plates so that said middle plate top surface is adjacent to said top plate bottom surface and said middle plate bottom surface is adjacent said bottom plate top surface;

a sample slot in said middle plate adapted to receive and hold an assay rod, said slot extending from said middle plate top surface to said middle plate bottom surface, said slot defining an assay rod chamber located between said top and bottom plates;

a flexible indentation in said top plate bottom surface extending away from said middle plate which defines a solution chamber between said top plate bottom surface and said middle plate top surface;

conduit means betwen said solution chamber and assay rod chamber for providing conduits through which solution can be transferred between said assay rod chamber and said solution chamber; and means associated with said assay rod chamber for introducing said sample into said assay rod chamber to interact with an assay rod located therein, said flexible top plate being deformable towards said middle plate at said indented portion defining said solution chamber to force solution through said conduit means to provide transfer of solution between said assay rod chamber and said solution chamber to provide treatment of said assay rod with said solution.

2. An assay card according to claim 1 wherein said conduit means includes an indentation in said top plate extending away from said middle plate which defines a channel between said top plate bottom surface and said middle plate top surface, said channel providing fluid connection between said solution reservoir and said assay rod reservoir.

3. An assay card according to claim 1 wherein said means for introducing sample into said assay rod chamber includes a flexible indentation in said top plate bottom surface extending away from said middle plate which defines a sample solution chamber; and a conduit connecting said sample solution chamber to said assay rod chamber whereby said flexible indentation may be deformed towards said middle plate to force sample solution from said sample solution chamber to said assay rod chamber.

4. An assay card according to claim 3 wherein said card includes a plurality of assay rod chambers and said means for introducing sample into said assay rod chambers further includes a flexible indentation in said top plate bottom surface extending away from said middle plate which defines a sample diluent chamber;

means for connecting said sample diluent chamber and sample solution to said plurality of assay chambers via common conduits;

means for varying the relative amounts of sample solution and diluent being passed through said common conduits to provide a test solution with varying concentrations; and to provide test solutions with varying concentrations of sample solution; and means for selectively controlling the flow of said test solution into said assay rod chambers to introduce test solutions having different sample concentrations therein into said assay rod chambers to provide testing of different sample concentrations by and assay rods.

5. An assay card according to claim 1 further including at least one reagent slot in said middle plate adapted to contain a reagent for treating said assay rod, said reagent slot extending from said middle plate top surface to said middle plate bottom surface, said slot defining a reagent chamber located between said top and bottom plates, said conduit means including means for providing conduits between said solution chamber, reagent chamber and assay rod chamber through which solution and reagent can be transferred to said assay rod chamber to provide treatment of said assay rod.

6. An assay card according to claim 5 wherein said conduit means includes:

a first flexible indentation in said top plate extending away from said middle plate which defines a first channel located between said top plate bottom surface and said middle plate top surface, said first channel having an inlet and an outlet;

means for connecting said first channel inlet to said solution chamber and means for connecting said first channel outlet to said reagent chamber;

a second flexible indentation in said top plate extending away from said middle plate which defines a second channel located between said top plate bottom surface and said middle plate top surface, said second channel having an inlet and an outlet; and means for connecting said second channel inlet to said reagent chamber and means for connecting said second channel outlet to said assay rod chamber to thereby provide fluid communication between said solution chamber, reagent chamber and assay chamber to allow transfer of said solution and reagent from said solution and reagent chambers to said assay rod chamber.

7. An assay card according to claim 6 wherein at least first and second reagent slots are provided in said middle plate to define first and second reagent chambers, said card further including means for selectively passing said solution from said solution chamber through said reagent chambers to provide selective transfer of reagents contained within said first and second reagnet chambers to said assay rod chamber.

8. An assay card according to claim 7 wherein said first reagent chamber is located closer to said front end of said middle plate than said second reagent chamber, said first channel and second channel being displaced longitudinally along opposite sides of said first and second reagent chambers, said means for selectively passing solution through said reagent chambers including:

a first solution transfer slot in said middle plate extending between said first reagent chamber and said first channel, said first solution transfer slot having an inlet connected to said first channel and an outlet connected to said first reagent chamber;

a second solution transfer slot in said middle plate extending between said first reagent chamber and said second channel, said second solution transfer slot having an inlet connected to said first reagent chamber and an outlet connected to said second channel;

a third solution transfer slot in said middle plate extending between said second reagent chamber and said first channel, said third solution transfer slot having an inlet connected to said first channel at a location spaced from said first solution transfer slot inlet and an outlet connected to said second reagent chamber; and a fourth solution transfer slot in said middle plate extending between said second reagent chamber and said second channel said solution transfer slot and flexible channels being arranged to provide selective passae of solution from said solution chamber through said reagent chambers by compression of the flexible channel indentations at selected well-defined locations to close said channels to thereby provide selective control of passage of solution through said channels and reagent chambers.

9. An assay card according to claim 8 wherein a pressure bar is passed from the front to rear of said card, said pressure bar extending laterally across said card and being positioned to compress the flexible indentations in said top plate against the top surface of said middle plate, said flexible channels, reagent chambers and solution transfer slots being arranged so that alternate only transfer of solution through said reagent chambers is provided as said pressure bar moves longitudinally from said card front end toward said card rear end.

10. An assay card system adapted for treating and analyzing a sample utilizng multiple assay rods comprising:
- a card having:
  - a solid bottom plate having a top surface, a front end, a rear end and sides extending between said front and rear ends;
  - a top plate having a bottom surface, a front end, a rear end and sides extending between said front and rear ends;
  - a middle plate having a top surface, a bottom surface, a front end, a rear end and sides extending between said front and rear ends, said middle plate being sandwiched between said bottom and top plates so that said middle plate top surface is adjacent to said top plate bottom surface and said middle plate bottom surface is adjacent said bottom plate top surface;
  - a sample slot in said middle plate adapted to receive and hold an assay rod, said slot extending from said middle plate top surface to said middle plate bottom surface, said slot defining an assay rod chamber located between said top and bottom plates;
  - a flexible indentation in said top plate bottom surface extending away from said middle plate which defines a solution chamber between said top plate bottom surface and said middle plate top surface;
  - conduit means between said solution chamber and assay rod chamber for providing conduits through which solution can be transferred between said assay rod chamber and said solution chamber; and
  - means associated with said assay rod chamber for introducing said sample into said assay rod chamber to interact with an assay rod located therein;
- a pressure bar positioned to extend laterally across said top plate, said pressure bar being positioned adjacent to said top plate to deform said flexible indentation toward said middle plate; and
- means for moving said pressure bar longitudinally relative said assay card to force solution through said conduit means to transfer solution from said solution chamber to said assay chamber to provide treatment of said assay rod with said solution.

11. An assay card system according to claim 10 wherein aid assay card further includes at least one reagent slot in said middle plate adapted to contain a reagent for treating said assay rod, said reagent slot extending from said middle plate top surface to said middle plate bottom surface, said slot defining a reagent chamber between said top and bottom plates, said conduit means including means for providing conduits between said solution chamber, reagent chamber and assay rod chamber through which solution and reagent can be transferred to said assay rod chamber to provide treatment of said assay rod.

12. An assay card system according to claim 11 wherein said conduit means in said assay card includes an indentation in said top plate extending away from said middle plate which defines a channel between said top plate bottom surface and said middle plate top surface, said channel providing fluid connection between said solution reservoir and said assay rod reservoir.

13. An assay card system according to claim 12 wherein said conduit means in said assay card includes:
- a first flexible indentation in said top plate extending away from said middle plate which defines a first channel located between said top plate bottom surface and said middle plate top surface, said first channel having an inlet and an outlet;
- means for connecting said first channel inlet to said solution chamber and means for connecting said first channel outlet to said reagent chamber;
- a second flexible indentation in said top plate extending away from said middle plate which defines a second channel located between said top plate bottom surface and said middle plate top surface, said second channel having an inlet and an outlt; and
- means for connecting said second channel inlet to said reagent chamber and means for connecting said second channel outlet to said assay rod chamber to thereby provide fluid communication between said solution chamber, reagent chamber and assay chamber to allow transfer of said solution and reagent from said solution and reagent chambers to said assay rod chamber.

14. An assay card system according to claim 13 wherein at least first and second reagent slots are provided in the middle plate of said assay card to define first and second reagent chambers, said solution chamber channels and reagent chambers being positioned in said card so that the movement of said pressure bar over said top plate provides selective passage of solution from said solution chamber through said reagent chambers to provide selective transfer of reagents contained within said first and second reagent chambers to said assay rod chamber.

15. A method for treating and analyzing a sample comprising the steps of:
- providing an assay card comprising:
  - a solid bottom plate having a top surface, a front end, a rear end and sides extending between said front and rear ends;
  - a top plate having a bottom surface, a front end, a rear end and sides extending between said front and rear ends;
  - a middle plate having a top surface, a bottom surface, a front end, rear end and sides extending between said front and rear ends, said middle plate being sandwiched between said bottom and top plates so that said middle plate top surface is adjacent to said top plate bottom surface and said middle plate bottom surface is adjacent said bottom plate top surface;
  - a sample slot in said middle plate adapted to receive and hold an assay rod, said slot extending from said middle plate top surface to said middle plate bottom surface, said slot defining an assay rod chamber located between said top and bottom plates;
  - a flexible indentation in said top plate bottom surface extending away from said middle plate which defines a solution chamber between said top plate bottom surface and said middle plate top surface;
  - conduit means between said solution chamber and assay rod chamber for providing conduits through which solution can be transferred between said assay rod chamber and said solution chamber;
- introducing said sample into said assay rod chamber to interact with an assay rod located therein; and deforming said flexible indentation in said top plate towards said middle plate to force solution through said conduit means to provide transfer of solution to said assay rod chamber by peristaltic action to provide treatment of said assay rod with said solution.

16. An assay card adapted for treating and analyzing a sample comprising:
   a card having a top surface, a bottom surface and an assay rod chamber located therein for housing an assay rod;
   a flexible structure protruding from the card top surface which defines a solution chamber;
   conduits means recessed in said card for providing conduits through which solutions can be transferred between said solution chamber and said assay rod chambr, said flexible structure being deformable to force solution between said assay rod chamber and said solution chamber to provide treatment of said assay rod with said solution.

17. An assay card according to claim 16 wherein flexible structures defining channels protrude from the card top surface to provide channels which may be closed by deforming said flexible channels, said channels being interconnected with said recessed conduit means to control the flow of solutions therethrough.

18. An assay card according to claim 17 wherein a plurality of recessed reagent chambers are provided in said card, said regent chambers, conduit means and flexible channels being arranged to provide selective transfer of solution through said reagent chambers when a pressure bar is passed across the top surface of the card.

19. An assay system comprising:
   a card having a longitudinal channel therein defining a reaction zone for housing an assay rod, said channel having an inlet and an outlet, said card further having one or more other longitudinal channels for housing reagent and wash solutions, said reagent and wash channels having an outlet and;
   conduit means for connecting the outlets of the reagent and wash channels to the inlet of the rod housing channel; and
   means for selectively transferring said reagent and wash solutions from the reagent and wash channels to the rod channel to provide reagents and wash solutions for reaction with and washing of the assay rod in the rod channel.

20. A card assembly for use in treating an assay rod with a plurality of treatment solutions to detect the presence of substances in a sample solution which engage in binding reactions with said assay rod comprising:
   a card having a top, a bottom and sides wherein said card includes a first channel located therein defining a reaction zone for housing a microassay rod, said first channel having an inlet and an outlet wherein sample solution can be selectively introduced into and removed from said reaction zone through said outlet;
   one or more second channels located in said card defining treatment solution reservoirs for containing treatment solutions and wherein each of said second channels has an outlet and wherein each of said channels includes a flexible top which is adapted to be deformed to provide movement of said treatment solutions to said second channel outlet by peristaltic action;
   conduit means for connecting the outlets of said second channels to the inlet of said first channel to provide liquid communication therebetween to allow selective transfer of said treatment solutions from said treatment solution reservoirs to said reaction zone by peristaltic action.

21. An assay card assembly according to claim 20 further including a magnetically or optically coded information strip containing information pertaining to the desired assay.

22. An assay system comprising the assay card assembly according to claim 20 and roller means for selectively transferring sample solution or treatment solution by peristaltic action into and out of said first and second channels.

23. An assay card assembly according to claim 20 wherein said card includes a top, a bottom, two sides, a first end and a second end, said first and second channels being parallel to each other and extending longitudinally between said first and second ends.

24. An assay card assembly according to claim 23 wherein said first channel outlet is located at said card second end and said second channel outlets are located at one end of said second channels.

25. A method for treating an assay rod with a plurality of treatment solutions to detect the presence of substances in a sample solution which engage in binding reactions with said assay rod, said method comprising the steps of:
   placing a assay rod in a reaction zone defined by a first channel located within a card, said first channel having an inlet and an outlet;
   introducing sample solution into said reaction zone through said first channel outlet for interaction with said assay rod; and
   introducing a treatment solution into said reaction zone through said first channel inlet, said treatment solution being transferred to said first channel inlet from a treatment solution reservoir defined by a second channel located within said card.

26. A method according to claim 25 wherein a plurality of treatment solutions are serially introduced and removed from said reaction zone.

27. A method according to claim 25 wherein said introduction and removal of solution from said reaction zone is accomplished by peristaltic action.

* * * * *